(12) United States Patent
Yamada

(10) Patent No.: US 11,925,481 B2
(45) Date of Patent: Mar. 12, 2024

(54) INFORMATION PROCESSING DEVICE, INFORMATION PROCESSING METHOD, AND PROGRAM

(71) Applicant: FUJIFILM Corporation, Tokyo (JP)

(72) Inventor: Kenta Yamada, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 425 days.

(21) Appl. No.: 17/241,077

(22) Filed: Apr. 27, 2021

(65) Prior Publication Data

US 2021/0248742 A1 Aug. 12, 2021

Related U.S. Application Data

(63) Continuation of application No. PCT/JP2019/035852, filed on Sep. 12, 2019.

(30) Foreign Application Priority Data

Oct. 29, 2018 (JP) .................. 2018-202949

(51) Int. Cl.
A61B 5/00 (2006.01)
G06F 18/2431 (2023.01)
(Continued)

(52) U.S. Cl.
CPC .......... A61B 5/7267 (2013.01); A61B 5/0077 (2013.01); A61B 5/4504 (2013.01);
(Continued)

(58) Field of Classification Search
CPC ... A61B 5/7267; A61B 5/0077; A61B 5/4504; A61B 5/7278; A61B 2576/00;
(Continued)

(56) References Cited

U.S. PATENT DOCUMENTS 7,809,173 B2 10/2010 Kitamura et al.
11,406,333 B2 * 8/2022 Goto .................... A61B 6/5205
(Continued)

FOREIGN PATENT DOCUMENTS

CN 103679133 3/2014
CN 107622281 1/2018
(Continued)

OTHER PUBLICATIONS

"International Search Report (Form PCT/ISA/210) of PCT/JP2019/035852," dated Dec. 10, 2019, with English translation thereof, pp. 1-4.
(Continued)

Primary Examiner — Juan A Torres
(74) Attorney, Agent, or Firm — JCIPRNET

(57) ABSTRACT

Information representing a physique of a subject is extracted from an image obtained by imaging the subject. A group in which the subject is classified is specified, using the extracted information representing the physique of the subject. Image data representing a medical image obtained by imaging the subject is input to a learned model corresponding to a specified group among learned models obtained for each group by machine learning using learning data for each group. Information representing an area extracted from the medical image is acquired, which is output from the learned model with the input.

7 Claims, 3 Drawing Sheets

(51) Int. Cl.
   *G06N 20/00* (2019.01)
   *G06T 7/00* (2017.01)
   *G06V 10/40* (2022.01)
   *G06V 10/764* (2022.01)
   *G06V 10/82* (2022.01)
   *G16H 30/20* (2018.01)
   *G16H 30/40* (2018.01)
   *G16H 50/20* (2018.01)
   *G16H 50/70* (2018.01)

(52) U.S. Cl.
   CPC ........ *A61B 5/7278* (2013.01); *G06F 18/2431* (2023.01); *G06N 20/00* (2019.01); *G06T 7/0012* (2013.01); *G06V 10/40* (2022.01); *G06V 10/764* (2022.01); *G06V 10/82* (2022.01); *G16H 30/20* (2018.01); *G16H 30/40* (2018.01); *G16H 50/20* (2018.01); *G16H 50/70* (2018.01); *A61B 2576/00* (2013.01); *G06T 2207/30008* (2013.01); *G06V 2201/033* (2022.01)

(58) Field of Classification Search
   CPC ... A61B 5/7485; A61B 5/1077; A61B 5/4887; A61B 2503/06; A61B 5/0073; A61B 5/055; A61B 5/742; G06F 18/2431; G06N 20/00; G06N 3/084; G06T 7/0012; G06T 2207/30008; G06V 10/40; G06V 10/764; G06V 10/82; G06V 2201/033; G06V 2201/03; G16H 30/20; G16H 30/40; G16H 50/20; G16H 50/70
   USPC ........................................................ 382/128
   See application file for complete search history.

(56) References Cited

U.S. PATENT DOCUMENTS

| | | | |
|---|---|---|---|
| 2014/0064577 A1 | 3/2014 | Kato et al. | |
| 2017/0319150 A1 | 11/2017 | Goto et al. | |
| 2017/0323447 A1* | 11/2017 | Tsukagoshi | A61B 6/467 |
| 2020/0118265 A1* | 4/2020 | Igarashi | A61B 5/055 |

FOREIGN PATENT DOCUMENTS

| | | |
|---|---|---|
| JP | 2004267450 | 9/2004 |
| JP | 2006175036 | 7/2006 |
| JP | 2007048172 | 2/2007 |
| JP | 2007105164 | 4/2007 |
| JP | 2007128127 | 5/2007 |
| JP | 2009070099 | 4/2009 |
| JP | 2014023640 | 2/2014 |
| JP | 2018134051 | 8/2018 |

OTHER PUBLICATIONS

"Written Opinion of the International Searching Authority (Form PCT/ISA/237) of PCT/JP2019/035852," dated Dec. 10, 2019,, with English translation thereof, pp. 1-8.

"Office Action of China Counterpart Application", dated Dec. 23, 2023, with English translation thereof, p. 1-p. 10.

* cited by examiner

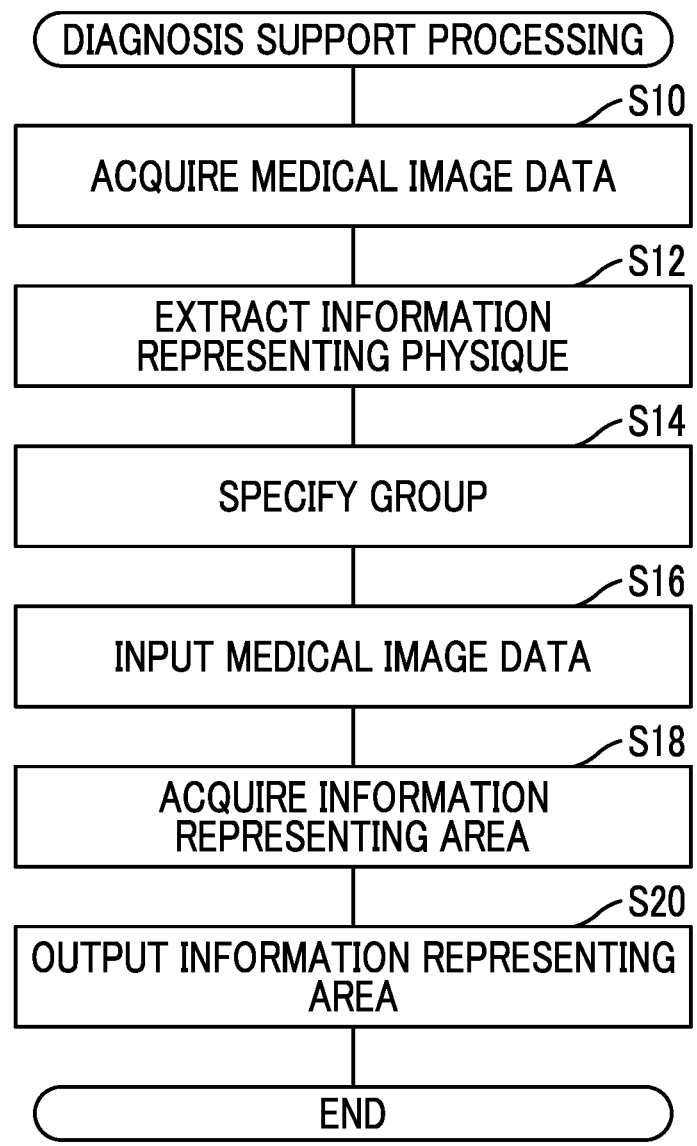

INFORMATION PROCESSING DEVICE, INFORMATION PROCESSING METHOD, AND PROGRAM

CROSS-REFERENCE TO RELATED APPLICATION

This application is a continuation of International Application No. PCT/JP2019/035852, filed on Sep. 12, 2019, which claims priority to Japanese Patent Application No. 2018-202949, filed on Oct. 29, 2018. The entire disclosures of both of the above-referenced applications are hereby incorporated by reference into the present application.

BACKGROUND

Technical Field

The present disclosure relates to an information processing device, an information processing method, and a program.

Related Art

A face detection method of detecting a face included in an input image while changing an inclination of a face to be detected is disclosed (refer to JP2007-128127A). In this face detection method, face detection is performed by any detection processing of first detection processing or second detection processing according to the inclination of the face to be detected.

An image processing device that detects a face from an input image using a face detection method according to a type of the input image is disclosed (refer to JP2009-070099A).

SUMMARY

The information processing device of the present disclosure comprises an extraction unit that extracts information representing a physique of a subject from an image obtained by imaging the subject, a specification unit that specifies a group in which the subject is classified, using the information representing the physique of the subject extracted by the extraction unit, an input unit that inputs image data representing a medical image obtained by imaging the subject to a learned model corresponding to the group specified by the specification unit among learned models obtained in advance for each group by machine learning using learning data for each group, and an acquisition unit that acquires information representing an area extracted from the medical image, which is output from the learned model with the input by the input unit.

BRIEF DESCRIPTION OF THE DRAWINGS

FIG. 5 is a flowchart showing an example of diagnosis support processing according to the embodiment.

DETAILED DESCRIPTION

Hereinafter, an embodiment of the present disclosure will be described in detail with reference to the drawings.

Figure 1:
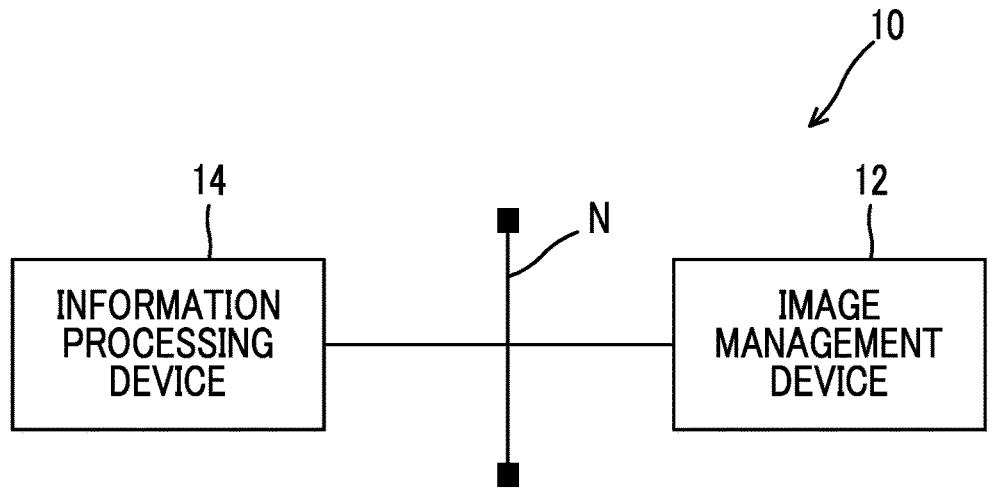
FIG. 1 is a block diagram showing an example of a configuration of a diagnosis support system according to an embodiment.

First, a configuration of a diagnosis support system 10 according to the present embodiment will be described with reference to FIG. 1. As shown in FIG. 1, the diagnosis support system 10 includes an image management device 12 and an information processing device 14. The image management device 12 and the information processing device 14 are each connected to a network N, and communication therebetween is possible through the network N. The image management device 12 stores image data (hereinafter referred to as "medical image data") representing a medical image obtained by imaging a subject via an imaging device that images a medical image such as computed tomography (CT) or magnetic resonance imaging (MRI). Examples of the image management device 12 include a picture archiving and communication system (PACS) and the like. The information processing device 14 supports the diagnosis using the medical image data stored in the image management device 12. Examples of the information processing device 14 include information processing devices such as a personal computer and a server computer.

Figure 2:
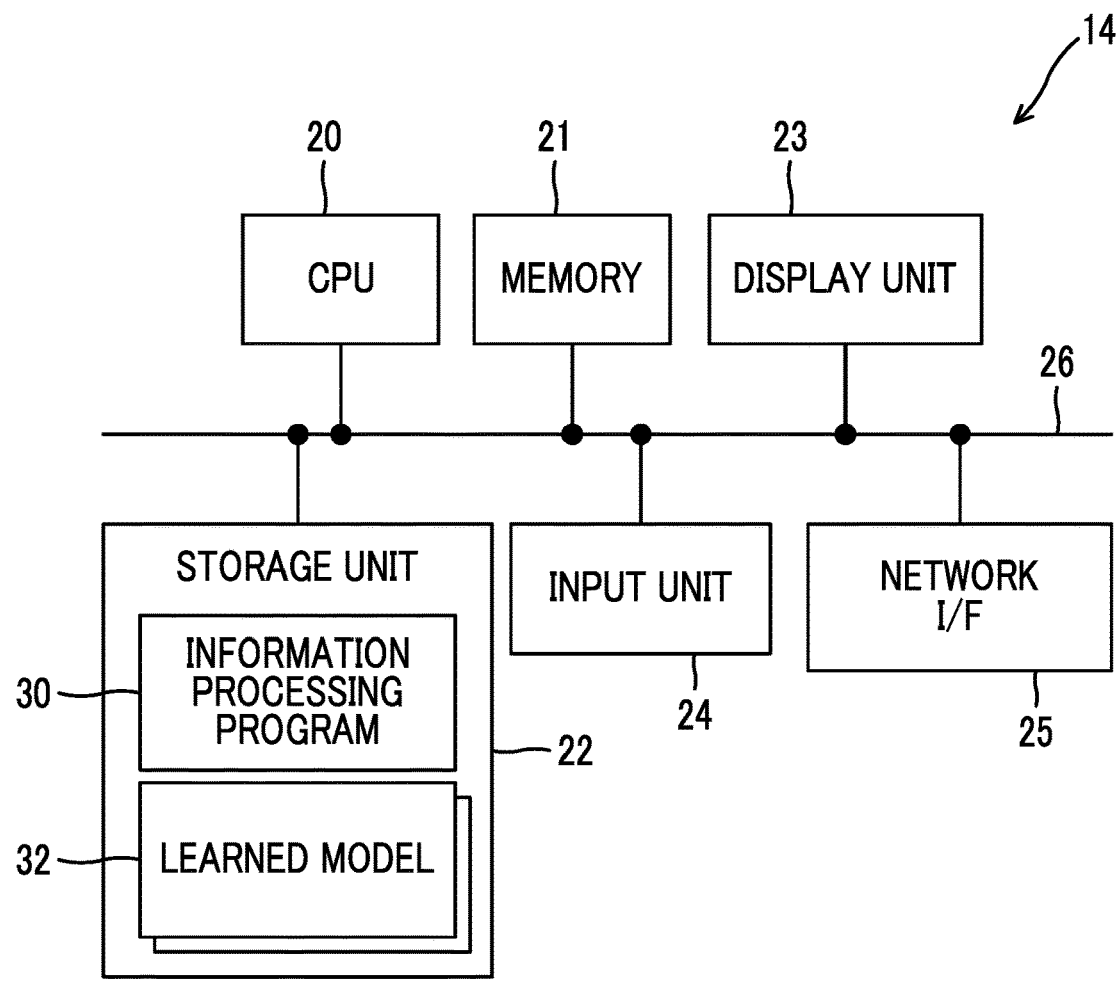
FIG. 2 is a block diagram showing an example of a hardware configuration of an information processing device according to the embodiment.

Next, a hardware configuration of the information processing device 14 according to the present embodiment will be described with reference to FIG. 2. As shown in FIG. 2, the information processing device 14 includes a central processing unit (CPU) 20, a memory 21 as a temporary storage area, and a nonvolatile storage unit 22. The information processing device 14 includes a display unit 23 such as a liquid crystal display, an input unit 24 such as a keyboard or a mouse, and a network interface (I/F) 25 connected to the network N. The CPU 20, the memory 21, the storage unit 22, the display unit 23, the input unit 24, and the network I/F 25 are connected to a bus 26.

The storage unit 22 may be a non-transitory recording medium such as a hard disk drive (HDD), a solid state drive (SSD), or a flash memory. The storage unit 22 stores an information processing program 30. The CPU 20 reads the information processing program 30 from the storage unit 22, develops the program in the memory 21, and loads and executes the developed information processing program 30.

Figure 3:
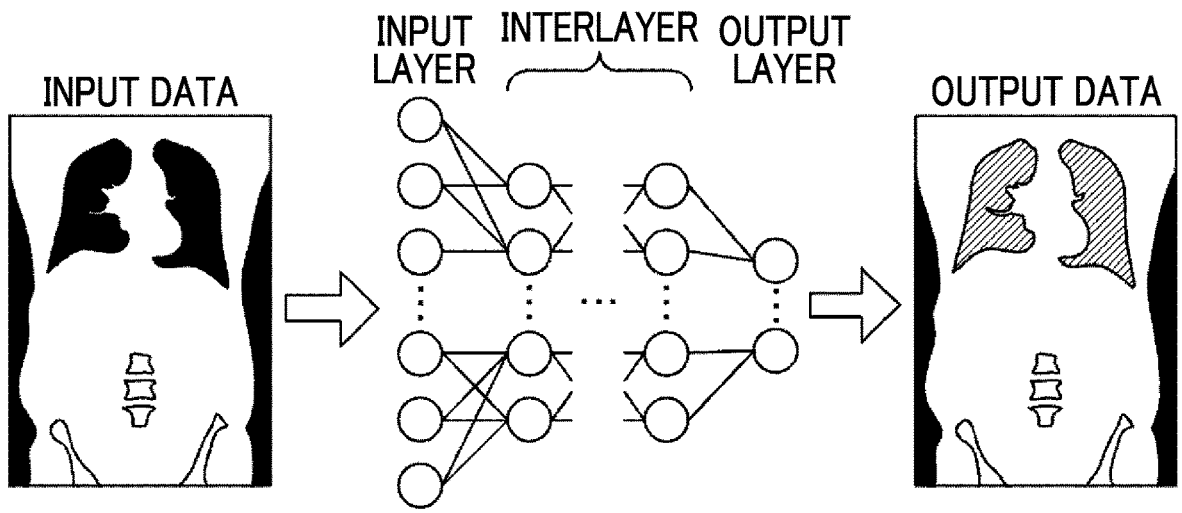
FIG. 3 is a diagram showing an example of a learned model according to the embodiment.

A plurality of learned models 32 (two in the present embodiment) are stored in the storage unit 22. The learned model 32 will be described with reference to FIG. 3. As shown in FIG. 3, a form in which a neural network including an input layer, a plurality of interlayers, and an output layer is applied will be described as an example of the learned model 32 in the present embodiment.

In the present embodiment, the learned model 32 is stored in the storage unit 22 for each group in which the subject is classified. Specifically, the storage unit 22 stores the learned model 32 corresponding to a group of children and the learned model 32 corresponding to a group of adults, which are classified by the age of the subject. The child as used herein means a child younger than a predetermined age, and the adult means a person equal to or older than the predetermined age. A boundary age between the child and the adult is not particularly limited and may be, for example, 15 years old or 18 years old. The number of groups in which subjects are classified is not limited to two and may be three or more.

As an example of input data, the medical image data obtained by imaging the subject via CT is input to the learned model 32. As an example of output data, information representing an area extracted from the medical image indicated by the input medical image data is output from the learned model 32. In the present embodiment, the learned model 32 extracts a lung area in the medical image indicated by the input medical image data and outputs image data representing an image in which the extracted lung area is filled with a predetermined color (for example, red). In FIG. 3, the extracted lung area is shown as a shaded area.

A case where the learned model 32 extracts both left and right lung areas will be described in the present embodiment, but the present invention is not limited thereto. The learned model 32 may extract any one of the left and right lung areas, an area other than the lungs, or a plurality of types of areas. Examples of the areas extracted by the learned model 32 include various organ areas, bone areas, blood vessel areas, and subcutaneous fat areas.

The learned model 32 is a model obtained in advance by performing machine learning for each group described above with a plurality of sets of medical image data and information representing the lung area in the medical image data as learning data (also referred to as teacher data). That is, the learned model 32 corresponding to the group of children is a model obtained in advance by performing the machine learning using the medical image data obtained by imaging the subject classified as a child and the information representing the lung area in the medical image data as the learning data. The learned model 32 corresponding to the group of adults is a model obtained in advance by performing the machine learning using the medical image data obtained by imaging the subject classified as an adult and the information representing the lung area in the medical image data as the learning data. In this case, an example of a method used for the machine learning includes an error backpropagation method or the like.

To obtain in advance means to obtain a model before selecting a selected model corresponding to the model and the specified group. The learning using the learning data of each group can be performed by this information processing device, or can be performed by an external device by sending the group information specified by this information processing device to the external device. Furthermore, the external device may acquire the physique information and classify into the groups before learning, and the information processing device may acquire or save the model learned by the external device.

Figure 4:
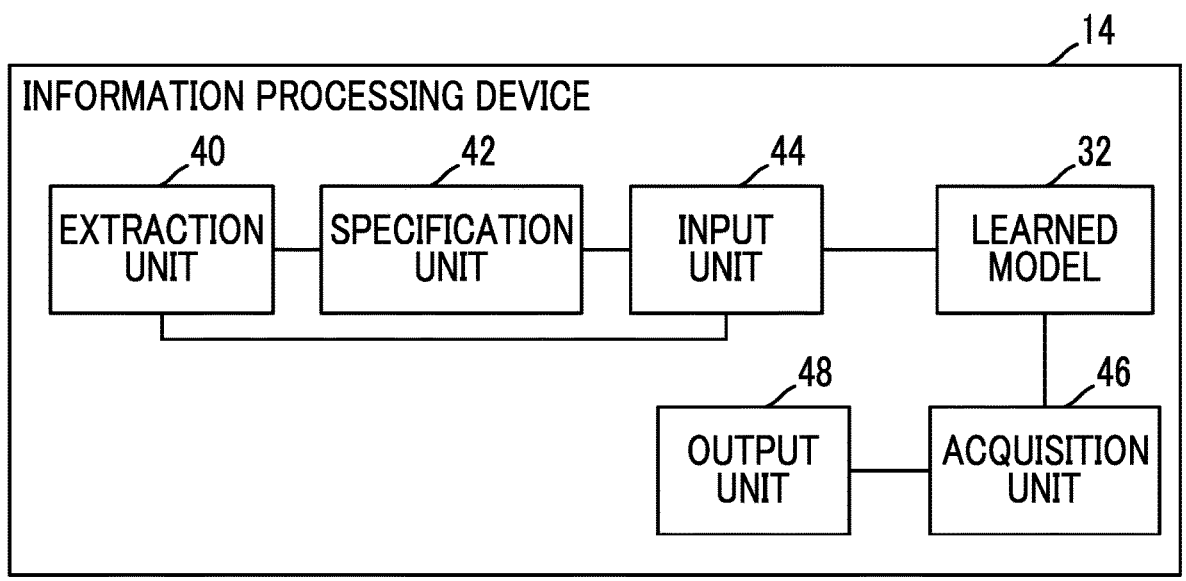
FIG. 4 is a block diagram showing an example of a functional configuration of the information processing device according to the embodiment.

Next, a functional configuration of the information processing device 14 according to the present embodiment will be described with reference to FIG. 4. As shown in FIG. 4, the information processing device 14 includes an extraction unit 40, a specification unit 42, an input unit 44, an acquisition unit 46, and an output unit 48. The CPU 20 executes the information processing program 30 to function as the extraction unit 40, the specification unit 42, the input unit 44, the acquisition unit 46, and the output unit 48.

The extraction unit 40 extracts information representing a physique of the subject from the medical image indicated by the medical image data acquired from the image management device 12 by the input unit 44 described below. In the present embodiment, the extraction unit 40 performs image analysis processing on the medical image to extract a skeleton of the subject as the information representing the physique of the subject. Specifically, for example, the bone area has a higher signal value in a CT image than other areas. Therefore, the extraction unit 40 extracts an area with a signal value that is equal to or higher than a threshold value from the medical image to extract the skeleton of the subject. In this case, the extraction unit 40 identifies the characteristics of the vertebrae and the pelvis in the extracted skeleton and identifies parts such as the head, chest, abdomen, and lower limbs.

The specification unit 42 specifies the group in which the subject is classified, using the information representing the physique of the subject extracted by the extraction unit 40. In the present embodiment, the specification unit 42 specifies whether the group in which the subject is classified are children or adults, using the skeleton of the subject extracted by the extraction unit 40. Specifically, for example, the specification unit 42 specifies whether the group in which the subject is classified is children or adults from a proportion of the head in the whole body of the skeleton of the subject. The proportion of the head in the whole body is about 15% to 25% for infants to elementary school students and is less than 15% for high school students or older. Therefore, it is possible to specify the group in which the subject is classified, with 15% as the threshold value, for example.

The input unit 44 acquires the medical image data from the image management device 12 and inputs the acquired medical image data to the learned model 32 corresponding to the group specified by the specification unit 42 among the learned models 32 stored in the storage unit 22. The acquisition unit 46 acquires the information representing the area extracted from the medical image output from the learned model 32 in response to the input by the input unit 44.

The output unit 48 outputs the information representing the area extracted from the medical image acquired by the acquisition unit 46 to the display unit 23. With this output, for example, an image in which the lung area is filled with a predetermined color is displayed on the display unit 23. A user diagnoses the subject using the image displayed on the display unit 23. The output unit 48 may output (store) the information representing the area extracted from the medical image acquired by the acquisition unit 46 to the storage unit 22 or output (transmit) the information to the image management device 12.

Next, an action of the information processing device 14 according to the present embodiment will be described with reference to FIG. 5. The CPU 20 executes the information processing program 30 to execute diagnosis support processing shown in FIG. 5. The diagnosis support processing shown in FIG. 5 is executed, for example, in a case where an instruction to execute the diagnosis support processing is input by the user through the input unit 24.

In step S10 in FIG. 5, the input unit 44 acquires the medical image data from the image management device 12. In step S12, the extraction unit 40 extracts the information representing the physique of the subject from the medical image indicated by the medical image data acquired by the processing of step S10, as described above. In step S14, the specification unit 42 specifies the group in which the subject is classified, using the information representing the physique of the subject extracted by the processing of step S12, as described above.

In step S16, the input unit 44 inputs the medical image data acquired in step S10 to the learned model 32 corresponding to the group specified by the processing of step S14 among the learned models 32 stored in the storage unit 22. In step S18, the acquisition unit 46 acquires information representing the area extracted from the medical image output from the learned model 32 in response to the input by the processing of step S16.

In step S20, the output unit 48 outputs the information representing the area extracted from the medical image acquired by the processing of step S18 to the display unit 23, as described above. In a case where the processing of step S20 ends, the diagnosis support processing ends.

As described above, according to the present embodiment, the group in which the subject is classified is specified by using the information representing the physique of the subject, and the image data representing the medical image obtained by imaging the subject is input to the learned model 32 corresponding to the specified group. The information representing the area extracted from the medical image output from the learned model 32 is acquired.

The medical image obtained by imaging the subject differs in an amount of radiation at the time of imaging, a size of an organ, an amount of fat, and the like, depending on whether the subject is a child or an adult. Specifically, the child is characterized by a smaller amount of radiation at the time of imaging, a smaller organ, and a smaller amount of fat than the adult. Therefore, it is possible to accurately extract the target area from the medical image by properly using the learned model 32 corresponding to the child and the learned model 32 corresponding to the adult as in the present embodiment.

According to the present embodiment, the information representing the physique of the subject is extracted from the medical image obtained by imaging the subject, and the group in which the subject is classified is specified by using the extracted information. Therefore, a dedicated image for extracting the physique of the subject is not required, and the user can specify the group without setting the group. As a result, it is possible to efficiently specify the group in which the subject is classified.

The case where the skeleton of the subject is applied as the information representing the physique of the subject has been described in the above embodiment, but the present invention is not limited thereto. For example, a form may be employed in which a body surface of the subject is applied as the information representing the physique of the subject. In this case, a form is exemplified in which the specification unit 42 derives an abdominal circumference, a shoulder width, and the like of the subject from the extracted body surface of the subject, and the group in which the subject is classified is specified from the derived physique such as the abdominal circumference, the shoulder width, and the like of the subject. In this case, it is possible to apply a criterion for metabolic syndrome as a threshold value for specifying a sex, for example.

In the above embodiment, the case where the group in which the subject is classified according to the age of the subject (in the above embodiment, children and adults) is applied as the group in which the subject is classified has been described, but the present invention is not limited thereto. For example, as the group in which the subject is classified, a form may be employed in which the group classified by the sex of the subject is applied, or a form may be employed in which the group classified by the race of the subject is applied. For example, as the group in which the subject is classified, a form may be employed in which the group classified by the species of the subject such as a human, a dog, or a cat is applied. The subject may be classified by a plurality of combinations of the above examples. In this case, a form is exemplified in which the subjects are classified in groups classified according to a combination of the age and the sex of the subjects, such as "child/male", "child/female", "adult/male", and "adult/female".

For example, a shape of a central hole in a pelvis is close to a triangle for men and a circle for women. Therefore, it is possible to specify the sex of the subject from the shape of the central hole of the pelvis. In addition, it is possible to specify whether the subject is a human or a non-human from a total number of bones, presence or absence of a tailbone, the number of teeth, and the like.

In the above embodiment, the case where the information representing the physique of the subject is extracted from the medical image has been described, but the present invention is not limited thereto. For example, a form may be employed in which the information representing the physique of the subject is extracted from an image captured by a non-medical imaging device. In this case, a form is exemplified in which the image analysis processing is performed on the image obtained by imaging the subject with a digital camera to extract the body surface of the subject from the image.

In the above embodiment, a form is exemplified in which a general-purpose learned model 32 common to all groups is prepared in advance and the general-purpose learned model 32 is used in a case where the group in which the subject is classified cannot be specified from the medical image.

In the above embodiment, it is possible to use the following various processors as a hardware structure of the processing units that execute various types of processing such as the extraction unit 40, the specification unit 42, the input unit 44, the acquisition unit 46, and the output unit 48. The various processors include a programmable logic device (PLD) which is a processor whose circuit configuration is changeable after manufacturing such as a field-programmable gate array (FPGA), a dedicated electric circuit which is a processor having a circuit configuration exclusively designed to execute specific processing such as an application specific integrated circuit (ASIC), and the like, in addition to the CPU which is a general-purpose processor that executes software (programs) to function as various processing units as described above.

One processing unit may be configured by one of the various processors or a combination of two or more processors of the same type or different types (for example, a combination of a plurality of FPGAs or a combination of a CPU and an FPGA). A plurality of processing units may be configured by one processor.

As an example of configuring the plurality of processing units with one processor, first, there is a form in which one processor is configured by a combination of one or more CPUs and software and the processor functions as the plurality of processing units, as represented by computers such as a client and a server. Second, there is a form in which a processor that realizes the functions of the entire system including the plurality of processing units with one integrated circuit (IC) chip is used, as represented by a system-on-chip (SoC) or the like. As described above, the various processing units are configured using one or more of the various processors as the hardware structure.

More specifically, it is possible to use a circuitry combining circuit elements such as semiconductor elements as the hardware structure of the various processors.

In the present embodiment, the form in which the information processing program 30 is stored (installed) in the storage unit 22 in advance has been described, but the present disclosure is not limited thereto. The information processing program 30 may be provided in a form of being recorded on a recording medium such as a compact disc read only memory (CD-ROM), a digital versatile disc read only memory (DVD-ROM), and a Universal Serial Bus (USB)

memory. The information processing program 30 may be downloaded from an external device through a network.

The present application claims the priority of JP2018-202949 filed on Oct. 29, 2018, the full text of which is incorporated herein by reference.

An object of the present disclosure is to provide an information processing device, an information processing method, and a program capable of accurately extracting a target area from a medical image.

The information processing device of the present disclosure comprises an extraction unit that extracts information representing a physique of a subject from an image obtained by imaging the subject, a specification unit that specifies a group in which the subject is classified, using the information representing the physique of the subject extracted by the extraction unit, an input unit that inputs image data representing a medical image obtained by imaging the subject to a learned model corresponding to the group specified by the specification unit among learned models obtained in advance for each group by machine learning using learning data for each group, and an acquisition unit that acquires information representing an area extracted from the medical image, which is output from the learned model with the input by the input unit.

The information representing the physique of the subject may be a skeleton of the subject.

The information representing the physique of the subject may be a body surface of the subject.

The image used for extracting the information representing the physique of the subject may be the medical image.

The group may be a group in which the subject is classified according to an age, a sex, a race, or a species of the subject.

An information processing method executed by a computer comprises extracting information representing a physique of a subject from an image obtained by imaging the subject, specifying a group in which the subject is classified, using the extracted information representing the physique of the subject, inputting image data representing a medical image obtained by imaging the subject to a learned model corresponding to the specified group among learned models obtained in advance for each group by machine learning using learning data for each group, and acquiring information representing an area extracted from the medical image, which is output from the learned model with the input.

A program causing a computer to execute the following processing of extracting information representing a physique of a subject from an image obtained by imaging the subject, specifying a group in which the subject is classified, using the extracted information representing the physique of the subject, inputting image data representing a medical image obtained by imaging the subject to a learned model corresponding to the specified group among learned models obtained in advance for each group by machine learning using learning data for each group, and acquiring information representing an area extracted from the medical image, which is output from the learned model with the input.

A non-transitory recording medium of the present disclosure records a program causing a computer to execute the following processing of extracting information representing a physique of a subject from an image obtained by imaging the subject, specifying a group in which the subject is classified, using the extracted information representing the physique of the subject, inputting image data representing a medical image obtained by imaging the subject to a learned model corresponding to the specified group among learned models obtained in advance for each group by machine learning using learning data for each group, and acquiring information representing an area extracted from the medical image, which is output from the learned model with the input.

The information processing device of the present disclosure comprises a memory and a processor connected to the memory. The processor is configured to extract information representing a physique of a subject from an image obtained by imaging the subject, specify a group in which the subject is classified by using the extracted information representing the physique of the subject, input image data representing a medical image obtained by imaging the subject to a learned model corresponding to the specified group among learned models obtained for each group by machine learning using learning data for each group, and acquire information representing an area extracted from the medical image, which is output from the learned model with the input.

According to the present disclosure, it is possible to accurately extract the target area from the medical image.

What is claimed is:

1. An information processing device comprising:
a memory; and
a processor coupling with the memory, the processor being configured to:
extract information representing a physique of a subject from an image obtained by imaging the subject;
specify a group in which the subject is classified, using the extracted information representing the physique of the subject;
input image data representing a medical image obtained by imaging the subject to a learned model corresponding to the specified group among learned models obtained for each group by machine learning using learning data for each group; and
acquire information representing an area extracted from the medical image, which is output from the learned model with the input image data.

2. The information processing device according to claim 1,
wherein the information representing the physique of the subject is a skeleton of the subject.

3. The information processing device according to claim 1,
wherein the information representing the physique of the subject is a body surface of the subject.

4. The information processing device according to claim 1,
wherein the image used for extracting the information representing the physique of the subject is the medical image.

5. The information processing device according to claim 1,
wherein the group is a group in which the subject is classified according to an age, a sex, a race, or a species of the subject.

6. An information processing method executed by a computer, comprising:
extracting information representing a physique of a subject from an image obtained by imaging the subject;
specifying a group in which the subject is classified, using the extracted information representing the physique of the subject;
inputting image data representing a medical image obtained by imaging the subject to a learned model corresponding to a specified group among learned models obtained for each group by machine learning using learning data for each group; and acquiring information representing an area extracted from the medical image, which is output from the learned model with the input image data.

7. A non-transitory computer-readable recording medium that records a program that is executable by a computer to perform a process, the process comprising:

extracting information representing a physique of a subject from an image obtained by imaging the subject;

specifying a group in which the subject is classified, using the extracted information representing the physique of the subject;

inputting image data representing a medical image obtained by imaging the subject to a learned model corresponding to a specified group among learned models obtained for each group by machine learning using learning data for each group; and acquiring information representing an area extracted from the medical image, which is output from the learned model with the input image data.

* * * * *